United States Patent [19]

Russo et al.

[11] Patent Number: 4,911,294
[45] Date of Patent: Mar. 27, 1990

[54] MEDICAL WASTE DISPOSAL SYSTEM

[76] Inventors: Anthony Russo, 1 Piping Brook La., Bedford, N.Y. 10506; Abel A. Russo, 23 Farview Rd., Carmel, N.Y. 10512

[21] Appl. No.: 194,493

[22] Filed: May 16, 1988

[51] Int. Cl.⁴ .............................................. B65D 83/10
[52] U.S. Cl. ..................................... 206/366; 220/403; 220/410; 220/1 T
[58] Field of Search ................. 206/366; 220/1 T, 403, 220/410

[56] References Cited

U.S. PATENT DOCUMENTS

| | | | |
|---|---|---|---|
| 3,057,506 | 10/1962 | Wetlesen | 220/1 T |
| 3,235,119 | 2/1966 | Smith | 220/1 T |
| 3,484,017 | 12/1969 | O'Donnell | 220/1 T |
| 3,648,875 | 3/1972 | Lundgren | 220/1 T |
| 3,997,072 | 12/1976 | Guth | 220/1 T |
| 4,126,241 | 11/1978 | Klosk | 220/1 T |
| 4,410,086 | 10/1983 | Simpson | 206/366 |
| 4,453,648 | 6/1984 | Harris et al. | 220/324 |
| 4,466,538 | 8/1984 | Gianni | 206/366 |
| 4,576,281 | 3/1986 | Kirksey | 206/370 |
| 4,637,545 | 1/1987 | Stewart | 232/43.2 |
| 4,657,139 | 4/1987 | Hanifl | 220/336 |
| 4,715,498 | 12/1987 | Hanifl | 206/366 |
| 4,722,472 | 2/1988 | Bruno | 229/128 |

OTHER PUBLICATIONS

Advertisement-Sage Products Inc., Copyright 1987, for In-Room Sharps Disposal System.
Advertisement-American Hospital Supply for Wall-Safe.
Advertisement-MEDX for Containers.
Advertisement-Post Medical, Inc. for Post Sharps Containment Systems.
Advertisement-Hemox for The Vault and The Vault Liner.

*Primary Examiner*—Joseph Man-Fu Moy
*Attorney, Agent, or Firm*—Eugene G. Reynolds

[57] ABSTRACT

A medical waste disposal system that allows for the "hands-off" disposal of medical waste. The system comprises a wall mounted outer container which is extended away from the wall upon which it is mounted. The outer container has an aperture for the receipt of medical waste and members extending from this aperture into its interior which automatically open an inner container when the inner container is inserted into the outer container. The automatic opening occurs when the members contact and force open tabs located on the inner container. These tabs are positioned to align with the members and are resiliently biased to the closed position so that the inner container automatically closes when it is removed from the outer container. The inner container may be removed without direct human contact by fully opening an access door located in the base of the outer container, thereby allowing the inner container to fall free of the system. The inner container falls into a receptacle which can be properly positioned due to the outer container's extension away from the wall upon which it is mounted.

19 Claims, 3 Drawing Sheets

MEDICAL WASTE DISPOSAL SYSTEM

BACKGROUND OF THE INVENTION

1. Field of the Invention

This invention relates to medical waste disposal systems in general and more particularly to a disposal system for use in medical facilities specifically designed to be a "hands-off" unit which virtually eliminates direct human contact with the potentially hazardous container used to collect and store contaminated items such as hypodermic needles and other sharp implements.

2. Description of the Prior Art

Medical waste disposal systems are known and are used to collect and store contaminated items. The need for such systems is well recognized and has become more acute with the proliferation of such highly contagious diseases such as the AIDS virus. These systems, however, subject users to possible infection when the users are required to come into contact with and handle the containers used for storing the medical waste. In particular, the containers are handled by users as contaminated items are placed therein and when the containers themselves are disposed of.

For example, the container disclosed in U.S. Pat. No. 4,722,472 must continuously be opened by hand in order to dispose of contaminated items. On each of these occasions the user is subjected to possible infection. Also, the container itself must be moved by hand when it is disposed of.

Similarly, the system disclosed in U.S. Pat. No. 4,715,498 requires that its inner container, in which contaminated items are stored, be manually closed once it is filled. The inner container is then removed by hand to be disposed of.

Even a system that tries to eliminate human contact with these potentially hazardous containers, such as the system disclosed in U.S. Pat. No. 4,637,545, requires that its container system be manually moved to a disposal cart and fails to provide for the closure of its interior container, thereby risking spillage of contaminated items and infection of its users.

SUMMARY OF THE INVENTION

It is therefore an object of the present invention to overcome the aforementioned disadvantages of prior art systems and provide a medical waste disposal system which allows for the disposal of a self closing container with virtually no direct contact by the individual disposing of the medical waste.

It is a further object of the present invention to provide a medical waste disposal system with an inner container for the storage of contaminated items that is automatically opened upon insertion into the system and is automatically closed when it is removed from the system.

It is a further object of the present invention to provide a medical waste disposal system that allows for the removal from the system of the inner container, used to store contaminated items, without direct human contact.

These and other objects of the present invention are achieved in a medical waste disposal system comprised of an outer container which is mounted on a wall. This outer container is provided with an elongated aperture through which contaminated items are placed. A restrictive barrier is placed at the aperture to prevent the insertion of a hand into the aperture. The outer container is set away from the wall upon which it is mounted. The extension from the wall allows an inner container to fall clearly through a door in the base of the outer container into a waiting receptacle when the door is fully opened. The outer container also has a member annexed to the edge of the aperture that extends into its interior. The inner container has a tab which is automatically opened by this member when the inner container is inserted into the outer container. The tab automatically closes when the inner container falls out of the outer container.

These and other novel features and advantages of the invention wil be described in greater detail in the following detailed description.

BRIEF DESCRIPTION OF THE DRAWINGS

In the drawings, wherein similar reference numerals denote similar elements throughout the several views thereof.

DETAILED DESCRIPTION OF THE INVENTION

Figure 1:
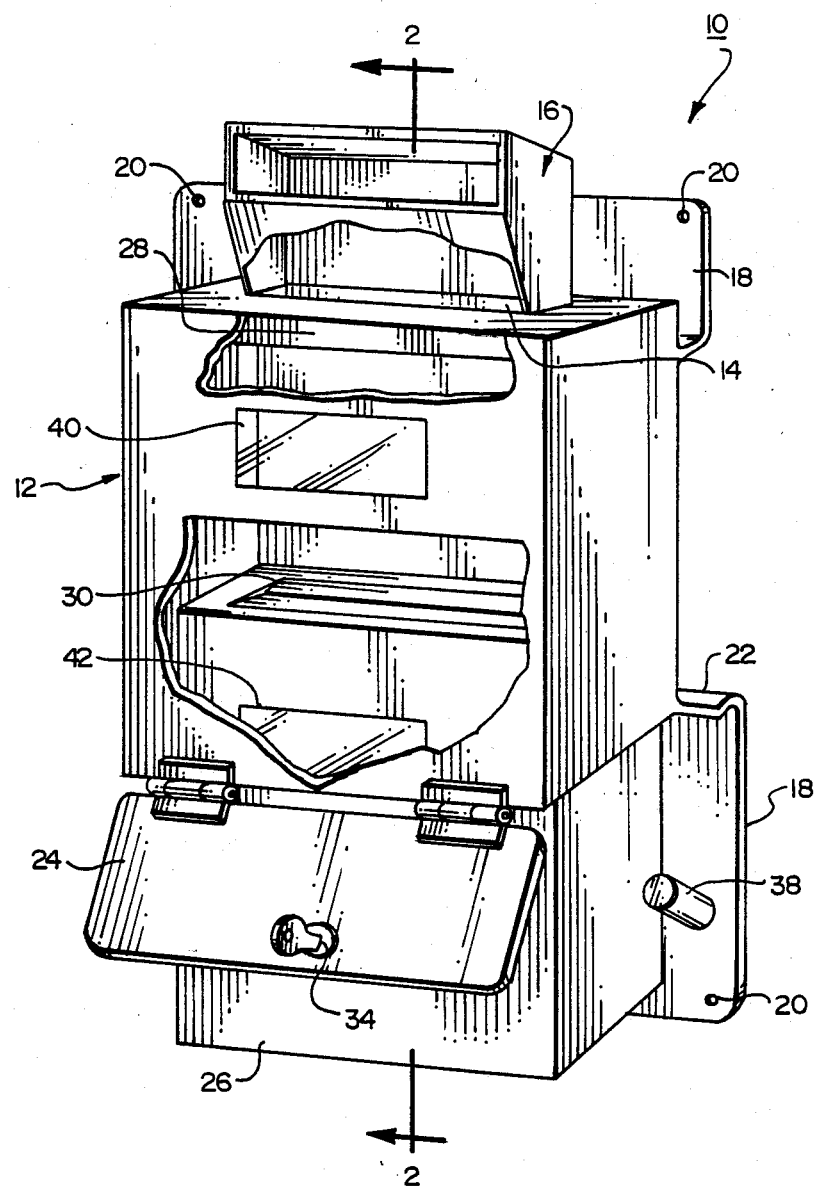
FIG. 1 is a cut-away view of the waste disposal system with the inner container partially inserted in the outer container.
Figure 2:
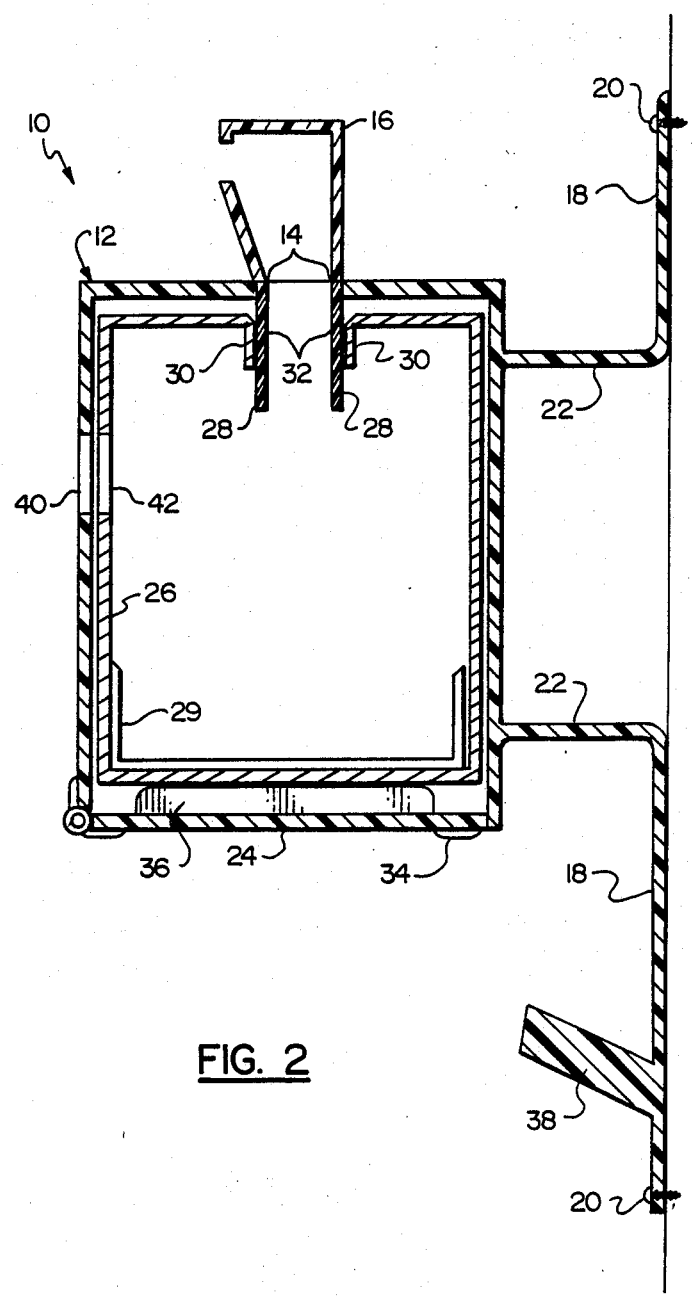
FIG. 2 is a cross-sectional view of the waste disposal system with the inner container fully inserted in the outer container.

Referring now to the drawings, and in particular to FIGS. 1 and 2, there is shown a medical waste disposal system, generally identified by reference numeral 10, which is designed to provide for the "hands-off" disposal of contaminated items.

The disposal system is comprised of an outer container 12. The outer container 12 is provided with an elongated aperture 14 through which contaminated items, such as hypodermic needles, are placed. The preferred embodiment of the invention is also provided with a barrier means 16, such as the raised cowl-like fixture shown in FIGS. 1 and 2, over the aperture 14 which prevents the insertion of a hand into the interior of the outer container 12.

The outer container 12 is rigid and may be formed from such material as molded plastic or metal. The outer container 12 is mounted on a wall. In the preferred embodiment, panels 18 abut the wall and are the mounting means through which screws 20 may be driven. The panels 18 are annexed to the outer container 12 by projections 22 which set the outer container 12 away from the wall. In the preferred embodiment of the invention the outer container 12, the panels 18 and the projections 22 are produced from the same mold and are continuous.

The outer container 12 is provided with an access door 24 in its base through which an inner container 26 is inserted into and removed from the outer container 12.

The outer container 12 also has a member 28 which is attached to the edge of the aperture 14 and which extends into the interior of the outer container 12. Although one member 28 is sufficient, the preferred embodiment of the invention has two members 28, attached to the two elongated edges of the aperture 14, which extend into the interior of the outer container 12 forming a channel through which contaminated items will pass.

The inner container 26 is of the same configuration, but of slightly smaller dimension, than the outer container 12. Although the containers shown in the accompanying drawings are boxlike in shape and represent the preferred embodiment of the invention, these drawing are illustrative in purpose and not restrictive. Other configurations of the two containers may be utilized in the present invention.

The inner container 26 is rigid and may be formed from such material as molded plastic or corrugated paper. The preferred embodiment of the invention has an inner container 26 comprised of transparent molded plastic. If the inner container 26 is comprised of corrugated paper, then a plastic insert 29 is provided for the inner base of said inner container 26. This plastic insert 29 prevents the leakage of the contents of the inner container 26.

As shown in FIGS. 1 and 2, inner container 26 is provided with a tab 30 which allows for the inner container 26 to be automatically opened upon its insertion into the outer container 12. This occurs because the tab 30 is positioned so that when the inner container 26 is inserted into the outer container 12, the tab 30 will come into contact with the member 28. When the inner container 26 is fully inserted into the outer container 12 the member 28 will force the tab 30 to open inwardly into the interior of the inner container 26. The member 28 will then extend into the interior of the inner container 26 and will hold the tab 30 open forming an inlet 32 in said inner container 26 which is in alignment with the aperture 14 of the outer container 12.

Only one tab 30 is necessary to provide the automatic opening feature of the present invention. The preferred embodiment of this invention, however, has two tabs 30 which are forced open by the two members 28 of the preferred embodiment.

The inner container 26 is also provided with means for resiliently biasing the tab 30 closed when the tab 30 is no longer held open by the member 28. This feature allows the tab 30 to automatically close when the inner container 26 is removed from the outer container 12.

The ability of the inner container 26 to automatically open and close upon insertion into and removal from the outer container 12 is a feature unique to the present invention and eliminates a source of possible human infection present in other waste disposal systems.

Another important feature of the present invention is that removal and disposal of the inner container 26 may be accomplished without human contact with the inner container 26. This is done by the opening of the access door 24. The access door 24 may be provided with a lock 34 and may be slideable or, as shown in FIG. 3, may be hinged, which is the preferred embodiment of the invention.

When the access door 24 is opened, the inner container 26 will, as a result of its own weight, the weight of the contaminated items contained therein and the force of gravity, automatically drop out of the outer container 12 without assistance.

Figure 3:
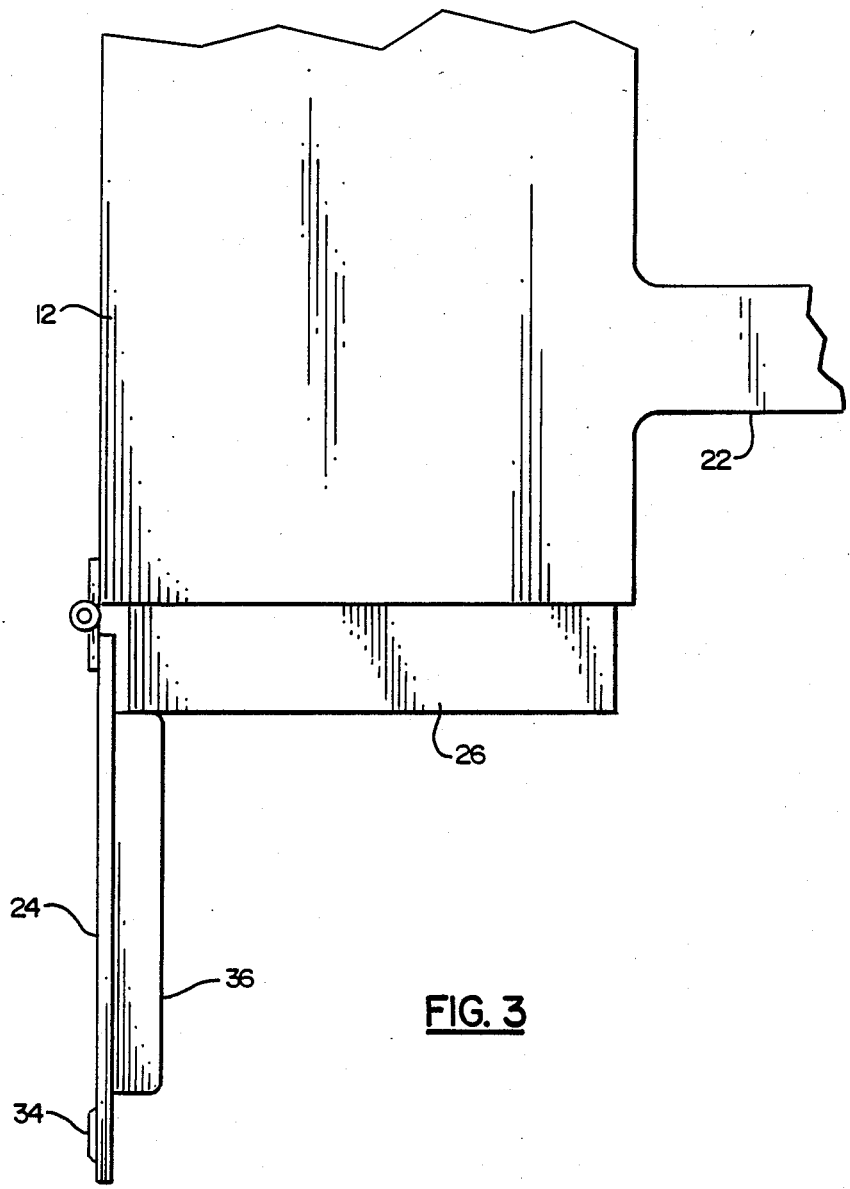
FIG. 3 is a side view of the base of the waste disposal system with its access door partially open.

As shown in FIG. 3, the fall of the inner container 26 is controlled by a ledge 36 which is attached to the inner side of the hinged access door 24. The ledge 36 will block the fall of the inner container 26 until the access door 24 is fully open. Accordingly, since the weight of the inner container 26 and its contents are insufficient to force the access door 24 fully open, the accidental dropping out of the inner container 26 is avoided.

The ledge 36 also assures that the inner container 26 is correctly inserted into the outer container 12 because when the access door 24 is closed the ledge 36 abuts the base of the inner container 26 and holds it in its proper position. Only one ledge 36 is necessary to control the fall of the inner container 26 when the access door 24 is open and to hold the inner container 26 in position when the access door 24 is closed. However, the preferred embodiment of the present invention has two ledges 36 which both perform these functions.

When the inner container 26 falls through the hole created by the opened access door 24 it drops into a receptacle, such as a barrel, which is placed below the disposal system. Although the receptacle is not part of the present invention, its proper placement could not be accomplished without the use of the projections 22 which set the outer container 12 away from the wall upon which it is mounted. Without the projections 22 the outer container 12 would sit flush against the wall. In this position the fall of the inner container 26 would be obstructed by the edge of the receptacle as well as the wall itself. The preferred embodiment of the invention also includes hooks 38 on the panels 18. The hooks 38 are positioned below the level of the access door 24 and may be used to hold a receptacle, such as a plastic bag, which is used to catch the inner container 26 as it falls out of the outer container 12.

Finally, the preferred embodiment of the present invention includes a window 40 in the side of the outer container 12 which permits an observer to determine when the inner container 26 is full. This observation can be made because in the preferred embodiment of the invention the inner container 26 is made of a transparent plastic through which the level of its contents may be observed. In the event, however, a different material such as corrugated paper is used to produce the inner container 26, then a second window 42 may be provided in the side of the inner container 26 which will align with the window 40 when the inner container 26 is fully inserted into the outer container 12 and will allow this observation to be made.

In the foregoing specification, the invention has been described with reference to a specific exemplary embodiment thereof. It will, however, be evident that various modifications and changes may be made thereunto without departing from the broader spirit and scope of the invention as set forth in the appended claims. The specification and drawings are, accordingly, to be regarded in an illustrative rather that in a restrictive sense.

What is claimed is:

1. A medical waste disposal system comprising
   an outer container having an elongated aperture permitting access to the interior of said outer container,
   a member attached to said outer container at an edge of said aperture and said member extending into the interior of said outer container,
   a removable inner container disposed within said outer container, said inner container having a tab positioned so that upon insertion of said inner container into said outer container said member will force said tab to open inwardly into the interior of said inner container and said member will extend into the interior of said inner container holding said tab in an open position and creating an inlet in said inner container which is in alignment with said aperture, and said inner container having means for resiliently biasing said tab to a closed position upon removal of said inner container from said outer container, and means for permitting insertion and removal of said inner container into and out of said outer container.

2. The disposal system recited in claim 1, further comprising barrier means positioned about the exterior of said aperture restricting access to the interior of said outer container.

3. The disposal system recited in claim 1, further comprising means for observing the level of contents in said inner container.

4. The disposal system recited in claim 3 wherein said means for observing the level of contents in said inner container comprises a first transparent window disposed in the side of said outer container and a second transparent window disposed in the side of said inner container such that when said inner container is fully inserted in said outer container, said first transparent window and said second transparent window are in alignment.

5. The disposal system recited in claim 3 wherein said inner container is comprised of transparent plastic and said means for observing the level of contents in said inner container comprises a transparent window disposed in the side of said outer container.

6. The disposal system recited in claim 1 wherein said means for permitting insertion and removal of said inner container comprises an access door.

7. The disposal system recited in claim 1 comprising two members, each member attached to said outer container at an elongated edge of said aperture and each member extending into the interior of said outer container parallel to the other member, and two tabs, each tab positioned on said inner container so that upon insertion of said inner container into said outer container each tab will be forced open by one of said members.

8. A medical waste disposal system comprising an outer container having an elongated aperture disposed in the top of said outer container, said aperture permitting access to the interior of said outer container, means for mounting said outer container on a wall, means for extending said outer container away from the wall upon which said outer container is mounted, a member attached to said outer container at an edge of said aperture and said member extending into the interior of said outer container, a removable inner container disposed within said outer container, said inner container having a tab disposed on the top of said inner container positioned so that upon insertion of said inner container into said outer container said member will force said tab to open inwardly into the interior of said inner container and said member will extend into the interior of said inner container holding said tab in an open position and creating an inlet in said inner container which is in alignment with said aperture, and said inner container having means for resiliently biasing said tab to a closed position upon removal of said inner container from said outer container, and an access door disposed in the base of said outer container such that when said door is completely opened said inner container falls through the hole created in said outer container by the complete opening of said door.

9. The disposal system recited in claim 8, further comprising barrier means positioned about the exterior of said aperture restricting access to the interior of said outer container.

10. The disposal system recited in claim 8, further comprising means for observing the level of contents in said inner container.

11. The disposal system recited in claim 10 wherein said means for observing the level of contents in said inner container comprises a first transparent window disposed in the side of said outer container and a second transparent window disposed in the side of said inner container such that when said inner container is fully inserted in said outer container, said first transparent window and said second transparent window are in alignment.

12. The disposal system recited in claim 10 wherein said inner container is comprised of transparent plastic and said means for observing the level of contents in said inner container comprises a transparent window disposed in the side of said outer container.

13. The disposal system recited in claim 8, further comprising means to control the fall of said inner container.

14. The disposal system recited in claim 13 wherein said means to control the fall of said inner container comprises a raised member disposed on the inner side of said access door.

15. The disposal system recited in claim 8 wherein said extension means comprises a projection disposed between said outer container and said mounting means.

16. The disposal system recited in claim 8 wherein said mounting means comprises a base attached to said extension means, said base abutting said wall and being secured to said wall.

17. The disposal system recited in claim 16, further comprising means for holding a receptacle for said inner container.

18. The disposal system recited in claim 17 wherein said means for holding a receptacle comprises a multiplicity of rods disposed on said mounting means below the level of said access door and extending away from said mounting means at an upward angle.

19. The disposal system recited in claim 8 comprising two members, each member attached to said outer container at an elongated edge of said aperture and each member extending into the interior of said outer container parallel to the other member, and two tabs, each tab positioned on said inner container so that upon insertion of said inner container into said outer container each tab will be forced open by one of said members.

* * * * *